United States Patent
Scott et al.

(10) Patent No.: US 7,517,342 B2
(45) Date of Patent: Apr. 14, 2009

(54) POLYMER COATED DEVICE FOR ELECTRICALLY MEDICATED DRUG DELIVERY

(75) Inventors: Neal Scott, Mountain View, CA (US); Jerome Segal, Mountain View, CA (US); Lih-Bin Shih, San Diego, CA (US); Terry L. Burkoth, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/425,170

(22) Filed: Apr. 29, 2003

(65) Prior Publication Data

US 2004/0220511 A1 Nov. 4, 2004

(51) Int. Cl.
*A61B 17/20* (2006.01)
(52) U.S. Cl. .................................. 604/501; 604/20
(58) Field of Classification Search ............ 604/20, 604/21, 500, 501, 103.02, 104–109, 114, 604/115–116, 119–120, 121; 606/190–194, 606/196; 600/372–375, 377, 381
See application file for complete search history.

(56) References Cited

U.S. PATENT DOCUMENTS

| | | | |
|---|---|---|---|
| 3,993,754 A | 11/1976 | Rahman et al. | |
| 4,411,648 A | 10/1983 | Davis et al. | |
| 4,709,698 A * | 12/1987 | Johnston et al. | 606/41 |
| 4,797,285 A | 1/1989 | Barenholz et al. | |
| 4,898,735 A | 2/1990 | Barenholz et al. | |
| 4,927,571 A | 5/1990 | Huang et al. | |
| 4,946,683 A | 8/1990 | Forssen | |
| 5,005,587 A * | 4/1991 | Scott | 607/122 |
| 5,019,394 A | 5/1991 | Hamaguchi et al. | |
| 5,034,001 A * | 7/1991 | Garrison et al. | 606/198 |
| 5,043,166 A | 8/1991 | Barenholz et al. | |
| 5,078,736 A * | 1/1992 | Behl | 623/1.15 |
| 5,282,785 A | 2/1994 | Shapland et al. | |
| 5,286,254 A | 2/1994 | Shapland et al. | |
| 5,415,869 A | 5/1995 | Straubinger et al. | |
| 5,419,763 A | 5/1995 | Hildebrand | |
| 5,449,513 A | 9/1995 | Yokohama et al. | |
| 5,458,568 A | 10/1995 | Racchini et al. | |

(Continued)

OTHER PUBLICATIONS

Sousa et al., New Frontiers in Cardiology Drug-Eluting Stents: Part I, May 13, 2003, 2274-2279.

(Continued)

*Primary Examiner*—Nicholas D Lucchesi
*Assistant Examiner*—Christopher D Koharski
(74) *Attorney, Agent, or Firm*—Kenyon & Kenyon LLP

(57) ABSTRACT

The present invention relates to a catheter with an expandable distal end for delivering one or more medicaments. The catheter is manufactured with materials of construction that allow the transfer of electrical energy from the proximal end of the catheter to the distal expandable end. The catheter also has a means for controlling or manipulating the expandable distal end to expand and contract into various configurations. The distal end of the catheter is processed by a specific method of manufacturing whereby the expandable distal end is coated with one or more layers of a hydrogel copolymer wherein at least one layer of which coating encapsulates one or more medicaments and zero or more charged carriers to facilitate the electrophoretic and electro-osmostic mobilities of the medicaments.

17 Claims, 4 Drawing Sheets

U.S. PATENT DOCUMENTS

| | | | |
|---|---|---|---|
| 5,498,238 A | 3/1996 | Shapland et al. | |
| 5,499,971 A | 3/1996 | Shapland et al. | |
| 5,505,700 A | 4/1996 | Leone et al. | |
| 5,507,724 A | 4/1996 | Hofmann et al. | |
| 5,510,103 A | 4/1996 | Yokohama et al. | |
| 5,527,282 A | 6/1996 | Segal | |
| 5,569,198 A | 10/1996 | Racchini | |
| 5,588,961 A | 12/1996 | Leone et al. | |
| 5,628,730 A | 5/1997 | Shapland et al. | |
| 5,648,090 A | 7/1997 | Rahman et al. | |
| 5,695,469 A * | 12/1997 | Segal | 604/104 |
| 5,704,908 A | 1/1998 | Holmann et al. | |
| 5,728,068 A | 3/1998 | Leone et al. | |
| 5,755,708 A | 5/1998 | Segal | |
| 5,776,486 A | 7/1998 | Castor et al. | |
| 5,800,392 A | 9/1998 | Racchini | |
| 5,807,306 A * | 9/1998 | Shapland et al. | 604/21 |
| 5,843,016 A | 12/1998 | Lugnani et al. | |
| 5,866,561 A | 2/1999 | Ungs | |
| 5,944,710 A * | 8/1999 | Dev et al. | 604/500 |
| 5,968,006 A | 10/1999 | Hofmann | |
| 6,009,345 A | 12/1999 | Hofmann | |
| 6,048,545 A * | 4/2000 | Keller et al. | 424/450 |
| 6,090,407 A | 7/2000 | Knight et al. | |
| 6,090,955 A | 7/2000 | Reszka et al. | |
| 6,149,641 A | 11/2000 | Ungs | |
| 6,219,577 B1 * | 4/2001 | Brown et al. | 604/20 |
| 6,223,075 B1 | 4/2001 | Beck et al. | |
| 6,346,233 B1 | 2/2002 | Knight et al. | |
| 6,461,637 B1 | 10/2002 | Rahman | |
| 2003/0100886 A1 | 5/2003 | Segal et al. | |
| 2003/0100887 A1 | 5/2003 | Scott et al. | |
| 2004/0267355 A1 | 12/2004 | Scott et al. | |
| 2004/0267356 A1 | 12/2004 | Scott et al. | |
| 2005/0038409 A1 | 2/2005 | Segal et al. | |
| 2005/0043680 A1 | 2/2005 | Segal et al. | |
| 2005/0054978 A1 | 3/2005 | Segal et al. | |
| 2005/0159704 A1 | 7/2005 | Scott et al. | |
| 2005/0240145 A1 | 10/2005 | Scott et al. | |

OTHER PUBLICATIONS

Sousa et al., New Frontiers in Cardiology Drug-Eluting Stents: Part II, May 6, 2003, 2383-2389.
Barry et al., Optimized Dosing for Drug Coated Stents, Mar. 27, 2003.
Babapulle et al., Coated Stents for the Prevention of Restenosis: Part I, Nov. 26, 2002, 2734-2740.
Babapulle et al., Coated Stents for the Prevention of Restenosis: Part II, Nov. 19, 2002, 2859-2866.
Grube et al., Taxus I, Oct. 24, 2002, 38-42.
Grube et al., Taxus III Trial, Oct. 22, 2002, 559-564.
Hwang et al., Physiological Transport Forces Govern Drug Distribution . . . , Apr. 5, 2001, 600-605.
Farb et al., Pathological Analysis of Local Delivery of Paclitaxol . . . , Apr. 5, 2001, 473-479.
Paclitaxel and Fluorescent Paclitaxel Conjugates, Jan. 2001.
Duncan et al., Polymer—drug conjugates, PDEPT and PELT:basic principles . . . , 2001, 135-146.
Creel et al., Arterial Paclitaxel Distribution and Deposition, Feb. 22, 2000, 879-884.
Perkins et al., Novel theraputic nano-particles (lipocores): lrapping poorly . . . ,Dec. 21, 1999, 27-39.
Crosasso et al., Preparation, characterization and properties of sterically . . . , Jul. 18, 1999, 19-30.
Wenk et al., Paclitaxel Partitioning into Lipid Bilayers, Nov. 1, 1995, 228-231.
Alkan-Onyuksel et al., A Mixed Micellar Formulation Suitable for the . . . , Aug. 30, 1993, 206-212.

* cited by examiner

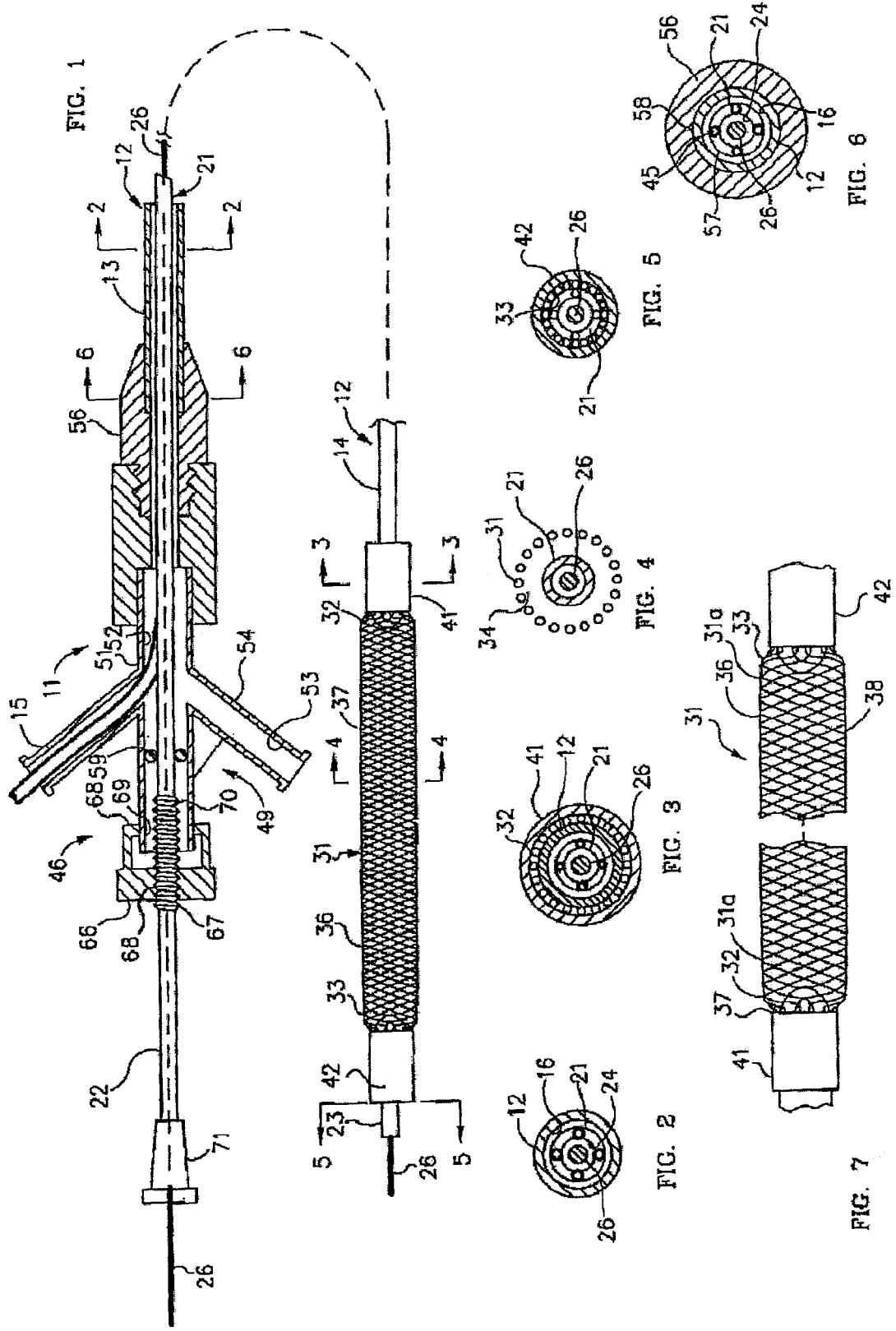

POLYMER COATED DEVICE FOR ELECTRICALLY MEDICATED DRUG DELIVERY

BACKGROUND OF THE INVENTION

Cardiovascular disease is commonly accepted as being one of the most serious health risks facing our society today. Diseased and obstructed coronary arteries can restrict the flow of blood and cause tissue ischemia and necrosis. After over two decades of investigation, the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Open heart surgery is, of course, very traumatic for patients. In many cases, less traumatic, alternative methods are available for treating cardiovascular disease percutaneously. These alternate treatment methods generally employ various types of percutaneous transluminal angioplasty (PTCA) balloons or excising devices (atherectomy) to remodel or debulk diseased vessel segments. A further alternative treatment method involves percutaneous, intraluminal installation of expandable, tubular stents or prostheses in sclerotic lesions.

A recurrent problem with the previous devices and PTCA procedures is their failure to maintain patency due to the growth of injured vascular tissue. This is known as "restenosis" and may be a result of the original injury to the vessel wall occurring during the angioplasty procedure. Pathologically restenosis represents a neointimal proliferative response characterized by smooth muscle cell hyperplasia that results in reblockage of the vessel lumen necessitating repeat PTCA procedures up to 35-50% of all cases. It has been generally accepted that certain therapeutic agents or medicaments may be capable of selectively inhibiting the growth of these hyperproliferating smooth muscle cells and thereby reduce the rate of restenosis after the primary interventional procedure.

Heretofore, various devices have been disclosed which may be used to deliver a therapeutic agent or medicament to a blood vessel while undergoing angioplasty. Balloon angioplasty catheters have been used to place and deliver various therapeutic agents or medicaments within human vessels. For example, in U.S. Pat. Nos. 5,112,305, 5,746,716, 5,681,281, 5,873,852, 5,713,863 and 6,102,904 disclose and claim a balloon catheter system with various injector plates mounted on the balloon for delivering a drug into an arterial segment.

Alternatively a standard angioplasty balloon may be coated with a substrate or polymeric material which either incorporates, or is then used to bond, certain medicaments or theraputic agents. These agents are then delivered to the desired therapeutic site by inflation of the balloon and diffusion of the medicament or therapeutic agent into the vessel wall. Only limited quantities of therapeutic agents can be delivered because of "wash-out" of the drug into the circulation during balloon placement and due to the limited time the inflated balloon can be left in place due to ischemia caused by the balloon.

In addition, previously disclosed methods of delivering drug to a site of treatment are described which utilize iontophoretic or electrophoretic means as disclosed in U.S. Pat. No. 5,499,971. Using these iontophoretic or electrophoretic means passive diffusion of the drug or medicament is enhanced by placing the medicament or therapeutic agent in close proximity to the site of treatment and then using electrical energy to augment delivery of the drug into the tissues or cells. These methods generally place the drug inside a balloon mounted distally on a catheter whereby the balloon is composed of a semi-porous material through which the drug can diffuse.

Additional devices have been disclosed which attempt to improve the depth of penetration into tissue by pressure driving a solution of the drug into the vessel wall through small orifices in the balloon material. There is, however, some evidence that high pressure "jetting" of a drug solution out of small pores close to the vessel lumen can in fact cause vessel wall injury. The development of double skinned, microporous (or weeping) balloons obviated this "jetting" effect to some extent, but diffusion of the drug into the vessel wall is still slow, and much of the drug can be lost through subsequent "washout effects". This method leads to limited amounts of drugs or therapeutic agents delivered to the tissues or cells. Furthermore, in all of these methods the balloon must be expanded and thereby restricts blood flow to the distal arterial segments while the balloon is in the expanded configuration thus limiting the time the drug delivering balloon can be clinically utilized.

There are also several disadvantages using either a stent or balloon catheter to deliver a therapeutic agent or medicament to a vascular segment. Regarding the therapeutic agent eluting stents, once the stent is deployed, there is no means outside of invasive surgical excision, to remove the eluting stent from the vascular segment. Therefore, stents or implanted prostheses with therapeutic agent eluting properties must be precisely calibrated to deliver an exact quantity of the therapeutic agent or medicament to the vascular segment upon stent deployment. Balloon catheters employed to deliver a therapeutic agent or medicament to a vascular segment have limitations including potential balloon rupture and ischemia due to balloon inflation limiting distal blood flow to the artery. This leads to tissue ischemia and potential necrosis. Even "perfusion" type angioplasty balloons used to delivery a therapeutic agent or medicament to the affected artery provide far less than physiological blood flow during balloon inflation and dwell times are limited by ischemia and tissue necrosis.

Additional devices have been disclosed which utilize catheter based multiple injecton ports to inject the drug directly into the vessel walls. Disadvantages of this system include potential injury to vessel walls, non-uniform drug delivery and the requirement that the drug must be carried either in the solubilized form or in fine suspensions which is a particular problem for drugs that are not water-soluble).

Recent studies have demonstrated the effectiveness of a number of agents (e.g., paclitaxel, rapamycin, Actinomycin D) on the prevention of unwanted cellular proliferation. These agents have proven efficacy in the treatment of cancer transplant rejection and restenosis following angioplasty. A major advantage of these agents is their high lipid solubility that causes tissue levels of these agents to remain high for an extended period of time since they cannot be rapidly cleared. However, the delivery of these lipophillic medicaments generally present formulation and transport challenges in aqueous media. Furthermore, they are less likely to permeate across hydrophilic boundries and cell membranes into tissue.

Recently various genetic agents such as DNA, RNA, and antisense oligonucleotides have shown promises in treating certain disease states. In-vivo delivery of these genetic agents is currently carried out with viral vectors or viral compounds may oftern lead to very undesirable side effects.

Thus, it can be seen that there is a need for a new and improved apparatus and method to selectively deliver a therapeutic agent or medicament to an arterial segment or other selected sites in a body, and which overcomes these disadvantages.

In general, it is an object of this present invention to provide a catheter coated with a hydrogel copolymer encapsulating one or more medicaments that is capable of delivering, by an active means, the medicament(s) to the vessel segment or obstruction.

In general, it is an object of this present invention to provide a catheter system whereby the catheter can be charged with an electrical energy and the electrical energy will facilitate the release of medicaments present in an encapsulated state in a hydrogel or polymer present on a portion of the catheter and augmenting transport of the medicaments into surrounding tissues.

In general, it is an object of this present invention to provide a method whereby the medicament is released from the hydrogel and transported into the surrounding tissues through the electrophoretic, iontophoretic or electro-osmotic processes, or the combination of the above processes. The delivery of the medicaments is can be without a charged carrier or with one or more charged carriers. The charged carriers can be charged surfactants, polyelectrolytes, liposomes or other charged entities including, but no exclusively, small ions.

Another object of the invention is to provide a method to deliver high concentrations of agents that are poorly soluble or insoluble in aqueous media to selected sites in the body including arteries, veins or other tubular structures, prosthetic devices such as grafts, and tissues such as, but not limited to, brain, myocardium, colon, liver, breast and lung.

Another object of the invention is to provide an apparatus and a method to deliver a wide range of medicaments with different degrees of solubility, molecular sizes and chemical structures These medicaments can be charged or neutral. The medicaments can include, but not exclusively, genetic agents Another object of the invention is to provide an apparatus and a method that can control the active release or diffusion of a medicament or therapeutic agent to minimize potential systemic effects and promote and maximize the delivery of the medicament or therapeutic agent into the surrounding tissue Another object of the invention is to provide an apparatus and a method to promote and maximize the penetration of a medicament or therapeutic agent into the surrounding tissues uniformly throughout the diseased area and to facilitate the binding to the tissue and thus promote a therapeutic effect.

Another object of the invention is to provide a apparatus and method that can promote the active release or diffusion of a medicament or therapeutic agent while simultaneously dilating an obstruction within a blood vessel or organ.

Another object of the invention is to provide a apparatus and method that can promote the active release or diffusion of a medicament or therapeutic agent while simultaneously allowing perfusion of blood or liquid to occur through the apparatus delivering the medicament or therapeutic agent.

SUMMARY OF THE INVENTION

The present invention relates to a catheter with an expandable distal end. The catheter is manufactured with materials of construction that allow the transfer of electrical energy from the proximal end of the catheter to the distal expandable end. The catheter also has a means for controlling or manipulating the expandable distal end to expand and contract into various configurations.

The distal end of the catheter is processed by a specific method of manufacturing whereby the expandable distal end is coated with one or more layers of a hydrogel copolymer at least one layer of which coating encapsulates one or more medicaments and zero or more charged carriers to facilitate the electrophoretic and electro-osmotic mobilities of the medicaments.

Electrophoresis, or iontophoresis, process describes the migration of a charged entity under the influence of an electrical field. Gel electrophoresis refers to use a porous water-swellable material as a supporting medium in this process with the specific purpose of minimizing the convection currents and diffusion in the free solutions. The supporting medium of a hydrogel is often used when critical separations of biologic components are required. The charged entities moving in the electrical field can be biological molecules such as proteins, DNA, carbohydrates, or oligonucleotides Often that the aqueous solution is buffered with various electrolytes. The electrolytes can be small ions, polyelectrolytes, charged or uncharged surfactants. All charged entities, regardless of the origin, migrate to the opposite electrode upon the application of the electrical field.

The successful migration of the desired medicaments out of the encapsulating hydrogel and into surrounding tissue in this invention, depends on many factors Migration is dependent on the charge and mass of the migrating entity. Other factors affecting migration and tissue penetration include the selection of the hydrogel and its chemical and physical characteristics, the selection of buffer systems, the selection of charged carriers, and the selection of electrical energy and time of discharge. In this invention, the proper selection of the electrophoretic conditions causes the medicaments encapsulated in the hydrogel to transport out of the gel and into the surrounding tissues. The medicaments may either be transported out of the gel by themselves or through the use of a charged carrier.

The medicaments are thought to be transported out of the hydrogel via several different mechanisms. If a medicament itself is charged, for example, proteins, DNA and RNA molecules which are negatively charged, the application of an electrical energy will cause these molecules to migrate to the opposite electrode and thus released from the hydrogel. If a medicament is uncharged the medicament is likely to migrate by electro-osmotic processes.

Electro-osmosis is a term applied to the process in which a liquid containing ions moves relative to a charged stationary surface. Electro-osmosis refers to the bulk movement of an aqueous solution past a stationary solid surface, due to an externally applied electrical field. Electro-osmosis generally requires the existence of a charged double-layer at the solid-liquid interface. This charged double layer results from an attraction between bound surface charges and ions in the passing fluid. The phenomenon of electro-osmosis has been applied in numerous ways, including as a means to augment the anodic delivery of (in particular) large, positively charged drugs, the transport numbers of which are often extremely small (and whose iontophoretic enhancement therefore depends heavily upon electro-osmosis) and to promote the migration of uncharged, yet polar, molecules, the passive permeation of which is typically very limited.

The present invention relates to the selection of charged carriers to facilitate electrophoretic mobility of medicaments, especially hydrophobic and water-insoluble medicaments. The charged carriers are surface active agents including, but not exclusively, surfactants, polyelectrolyts and phospholipids. . . . These surface active agents may also form micelles or vesicles promoting the lipophillic medicaments to be solubilized inside the micelles. The medicament may thus be released from the hydrogel as the charged micelles are transported out of the hydrogel upon the application of the electrical energy.

Another potential mechanism of medicament release from the hydrogel involves binding of the charged carrier onto the medicament molecules. This renders the medicament charged and capable of migrating in the electrical field. It is well known that surface active surfactants, either charged or uncharged, are very likely to bind strongly to biological molecules, such as proteins or DNA, and synthetic polyelectrolytes. The binding of a charged surfactant to a medicament molecule effectively increases the charge of the medicament and thus facilitate its electrical mobility.

The present invention relates to the delivery of charged or uncharged medicaments within the body of a patient. The invention uses electrophoretic mediated drug delivery with a specially designed catheter. The catheter has a metal mesh on its distal end that expands against a solid, tubular or hollow structure. The mesh is coated with one or more layers of hydrogel at least one layer of which contains at least one drug or medicament and zero or more charged carriers or surface active agents. When current is applied, the charged medicament or the charged carrier carrying one or more medicaments along with it, moves electrophoretically towards the opposite electode. This method is thus capable of moving drugs or medicaments that are either charged or uncharged using electrical energy.

The hydrogel used in the present invention is a block copolymer consisting of alternating hydrophilic and hydrophobic blocks. A hydrogel is a material that swells in water and has certain structural integrity, and resists flow, upon swelling. A hydrogel forms a network type of structure in water consisting of pores and crosslinks, and is often characterized by its water content, or alternatively the pore size. The pores serve as the water channels for the charged particles to move during the electrophoretic process while the crosslinks serve to maintain the network stability. The greater the water content, the bigger the pores.

The hydrogel copolymer used in the current invention possesses the following characteristics. It forms strong adhesion with the catheter metal surface. The adhesion must sustain the repeatedly contraction and expansion of the catheter mesh during application. Furthermore, the hydrogel must possess certain tensile and mechanical properties that preserve the coating integrity during the contraction and expansion operations of the catheter mesh.

The water content, and thus the pore size, of the hydrogel is one of the critical factors affecting the electrophoretic behaviors of the charged particles. The water content of the hydrogel may be controlled by controlling the ratio of the hydrophilic block to the hydrophobic block during hydrogel fabrication. Other chemical characteristics, such as the degree of hydrophilicity, and physical characteristics such as mechanical strength, may be also be controlled by the ratio and the size of the hydrophilic and the hydrophobic blocks in the block copolymer. The flexibility to adjust the chemical nature of the hydrogl network makes it possible to encapsulate a wide range of medicaments of different chemical and physical properties.

Furthermore, the hydrogel block copolymer is a thermoplastic copolymer soluble in certain polar solvents. Conventional coating methods can be used to apply the viscous polymer solution to the catheter surface to form a thin layer of coating. The polymer solution coagulates and precipitates in the presence of a non-solvent. If water is used as coagulant, only the hydrophobic blocks collapse and coagulate, but the hydrophilic blocks swell in water, in the presence of water, the polar solvent is replaced and the polymer solution turns into a swollen gel network structure. The coating may be one layer or multiple layers with the same or different hydrogel copolymer. Each layer may or may not contain medicaments. In the event of a multiple layer hydrogel coating, the introduction of the water to completely coagulate the copolymer is at the final step.

There are several ways a medicament, or medicaments, may be introduced into the hydrogel and thus onto the catheter. For example, the hydrogel coating may be preformed on the catheter surfaces and the coated catheter immersed into a concentrated drug solution. The hydrogel coating will absorb medicaments until it reaches an equilibrium state. Alternatively, the medicaments, either in the solid form or in a solution form, may be mixed directly into the polymer solution prior to coating, which is then followed by the coating and coagulation steps outlined above. This latter compounding method allows very high concentrations of medicaments to be placed into the hydrogel coating.

The delivering of medicaments by the present invention and methods generally comprises the steps of advancing a catheter or medical device generally including a distal expansion member and advancing the expansion member to an obstruction within a vessel or to the desired site of treatment. At this time the clinician applies forces on the expansion member causing the expansion member to become fully expanded wherein the expansion member contacts the surrounding tissue. An electrical means is then employed which actively activates the encapsulated medicaments and zero or more charged carriers within the hydrogel causing the medicaments to be transported out of the hydrogel and delivered into the surrounding tissues.

BRIEF DESCRIPTION OF THE DRAWINGS

FIG. 1 is a side-elevational view partially in section of a medicament delivery device incorporating a copolymer hydrogel encapsulating a therapeutic agent.

FIG. 2 is a cross-sectional view taken along the line 2-2 of FIG. 1.

FIG. 3 is a cross-sectional view taken along the line 3-3 of FIG. 1.

FIG. 4 is a cross-sectional view taken along the line 4-4 of FIG. 1.

FIG. 5 is a cross-sectional view taken along the line 5-5 of FIG. 1 demonstrating the electrical connection means.

FIG. 6 is a cross-sectional view taken along the line 6-6 of FIG. 1.

FIG. 6a is a cross-sectional view taken along the line 6-6 of FIG. 1 also demonstrating the electrical connection means.

FIG. 7 is a greatly enlarged view of a portion of the dilatation and medicament delivery device in a partially expanded state.

DETAILED DESCRIPTION OF THE DRAWINGS

Figure 8A:
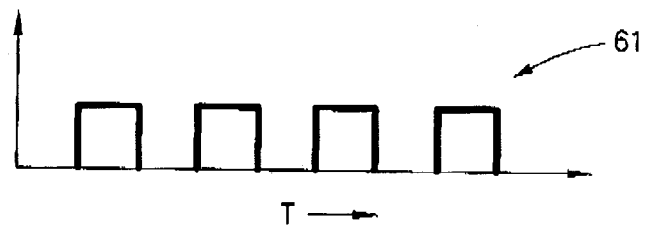
FIGS. 8a-8f depict a variety of electric waveforms for use in iontophoresis and electrophoresis with the catheter and distal mesh of the present invention.
Figure 8B:
Figure 8C:
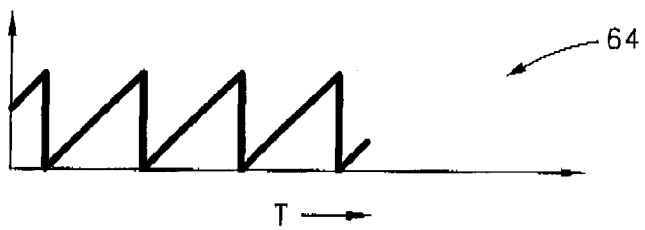
Figure 8D:
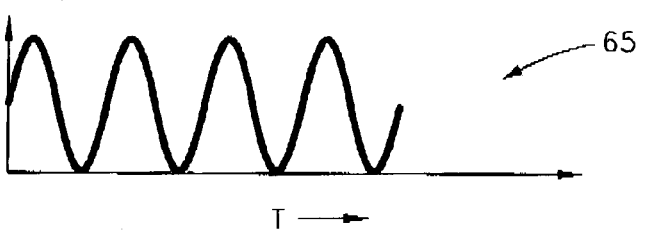
Figure 8E:
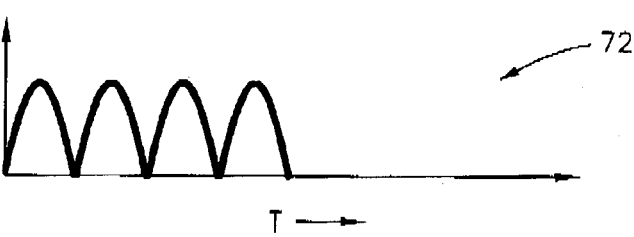
Figure 8F:
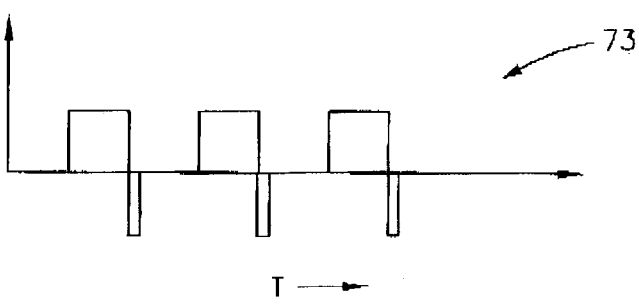
Figure 9:
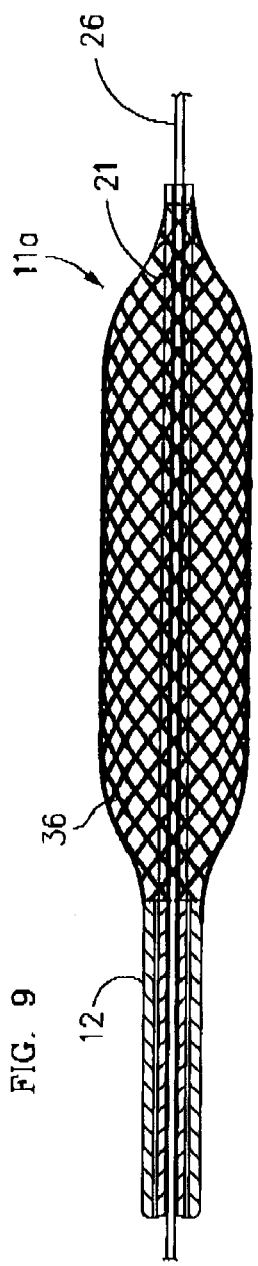
FIG. 9 is a side-elevational view of the distal extremity of the device shown in FIGS. 1-9 showing the distal extremity with the expansion member in an expanded condition showing the hydrogel with encapsulated medicaments coated on the distal expansion member.

In general, the present invention relates generally to devices that are used to dilate and dispense a medicament or therapeutic agent to an obstruction within a stenotic segment of a vessel or other tubular structure. The device is comprised of an cylindrical expansion member to be disposed in an obstruction in a vessel carrying flowing blood. The cylindrical expansion member has first and second ends and an intermediate portion between the first and second ends. The cylindrical expansion member also has a flow passage extending therethrough with a diameter and a longitudinal central axis. The diameter of the flow passage is a variable with movement of the first and second ends relative to each other along the longitudinal central axis from a diametrically contracted position to a diametrically expanded condition. The cylindrical expansion member is comprised of a plurality of flexible elongate elements each of which extends helically about the longitudinal extending central axis. The flexible elongate elements are coated with a copolymer hydrogel encapsulating a therapeutic agent, medicaments, drugs, pharmaceuticals, plasmids, genes, double and single stranded DNA or other agents. For the purposes of this application, the terms copolymer hydrogel encapsulating a medicament or therapeutic agent, drugs, pharmaceuticals, plasmids, genes or other agents, will be used to encompass all the particular agents described herein. It is also contemplated that the copolymer hydrogel encapsulated medicament or therapeutic agent may be incorporated with a non-medicament substrate that has been previously or simultaneously coated on the flexible elongate elements.

Means are provided for engaging the first and second ends of said cylindrical expansion member for retaining said first and second ends in contracted positions. Altering means are provided for causing relative axial movement of the first and second ends towards each other to cause the intermediate cylindrical portion of the expansion member to contract longitudinally and to expand diametrically by causing the flexible elongate elements in the intermediate portion of the cylindrical member to move closer to each other expanding the diametric dimensions of the cylindrical expansion member thereby allowing it to contact the vessel wall and enable it to dilate an obstruction within the vessel. Flexible elongate elements at the first and second ends of the cylindrical expansion member remain contracted around and within first and second means and are thereby prevented from moving closer which maintains spacing between the flexible elongate members so that blood in the vessel can continue to flow through the first and second ends and through the flow passage in the cylindrical expansion member while the cylindrical expansion member is in engagement with vessel wall and dilating an obstruction within the vessel.

More in particular as shown in FIGS. 1-7 of the drawings, the mechanical dilatation and medicament delivery device 11 shown therein consists of a first or outer flexible elongate tubular member 12 having proximal and distal extremities 13 and 14 with the flow passage 16 extending from the proximal extremity 13 to the distal extremity 14. FIGS. 2, 3, 5, and 6 are provided to demonstrate the electrical conduction means extending from the proximal connector and engaged to the distal expansion member 31. A second or inner flexible tubular member 21 is coaxially and slidably disposed within the flow passage 16 of the first or outer flexible elongate tubular member 12 and is provided with proximal and distal extremities 22 and 23 with a flow passage 24 extending from the proximal extremity 22 to the distal extremity 23. Since the flexible elongate elements of the dilating member are made of a metallic material such as stainless steel, elgiloy or other conductive material, an electrical lead(s) 45 (FIG. 6) can be connected to the mesh to make it part of the circuit. The electrical lead can either run along or within one of the lumens of the catheter or can be in the form of a braid that is made of a conductive material and have generally functions to provide reinforcement to the catheter shaft. In the example shown in FIG. 6, the electrical leads 45 are located within second or inner flexible tubular member 21. A second electrode could be placed on the distal tip of the catheter via a small band with its electrical lead running down one of the lumens to the proximal end of the catheter. Alternatively, the electrical lead could be engaged to the patient's skin or could be the guidewire over which the catheter is routinely advanced.

A guide wire 26 of a conventional type is adapted to be introduced through the flow passage 24 in the inner flexible elongate tubular member for use in guiding the mechanical dilatation and medicament delivery device 11 as a over-the-wire design as hereinafter described. The guide wire 26 can be of a suitable size as for example 0.010"-0.035" and can have a suitable length ranging from 150 to 300 centimeters. For example, the first or outer flexible elongate tubular member 12 can have an outside diameter of 0.6-3 millimeters with a wall thickness of 0.12 millimeters to provide a flow passage of 0.75 millimeters in diameter. Similarly, the second or inner flexible elongate tubular member 21 can have a suitable outside diameter as for example 0.6 millimeters with a wall thickness of 0.12 millimeters and a flow passage 24 of 0.45 millimeters in diameter. The flexible elongate tubular members 12 and 21 can be formed of a suitable plastic as for example a polyimide, polyethylene, Nylon or polybutylterphalate (PBT).

In accordance with the present invention an essentially cylindrically shaped expansion member 31 is provided which has a first or proximal end 32 and a second or distal end 33 with a central or inner flow passage 34 extending from the proximal end 32 to the distal end 33 along a longitudinally extending central axis and has a diameter which is a variable as hereinafter described. The cylindrically shaped expansion member 31 is comprised of a plurality of flexible elongate elements or filaments 36 each of which extends helically about the longitudinally extending central axis. The flexible elongate elements 36 are formed of suitable materials which can be utilized in the human blood as for example stainless steel, Nitinol, Aermet™, Elgiloy™ or certain other plastic fibers. The flexible elongate elements 36 can have a suitable diameter as for example 0.001 to 0.010 inches or can be configured as a round, elliptical, flat or triangular wire ribbon. A plurality of the flexible elongate elements 36 have a first common direction of rotation about the central axis as shown in FIGS. 1 and 7 are axially displaced relative to each other and cross a further plurality of the flexible elongate elements 36 also axially displaced relative to each other but having a second common direction of rotation opposite to that of the first direction of rotation to form a double helix or braided or mesh-like cylindrical expansion member with the crossing of flexible elongate elements 36 occurring in the area of contact between the flexible elongate elements to form openings or interstices 37 therebetween. Thus the flexible elongate elements 36 form an expansion member 31 which provides a central or inner flow passage 34 which is variable in diameter upon movement of the first and second ends of the expansion member 31 relative to each other along the longitudinally extending central axis.

Means is provided for constraining the first and second or proximal and distal ends 32 and 33 of the expansion member 31 and consists of a first or proximal collar 41 and a second or distal collar 42. The first and second collars 41 and 42 are formed of a suitable material such as a polyimide.

Typically the distance between the first and second collars 41 and 42 can range from between 5 to 150 millimeters. Typically the distal end 23 of the second or inner flexible elongate tubular member 21 extends approximately 5-170 millimeters beyond the distal extremity 14 of the first or outer flexible elongate tubular member 12.

It can be seen that by moving the first or outer flexible elongate tubular member 12 and the second inner flexible elongate tubular member 21 axially with respect to each other, the first and second ends of the expansion member 31 are moved towards each other causing the elongate elements or filaments 36 of an intermediate portion of the cylindrical expansion member between the first and second ends to move closer to each other to cause these flexible elongate elements to move into apposition with each other and to expand in a first radial direction the intermediate portion of the cylindrical expansion member 31 (FIG. 7) and to cause the diameter of the central flow passage 34 to increase. The portions of the expansion member 31 immediately adjacent the first and second collars 41 and 42 remain restrained by the collars 41 and 42 causing the flexible elongate elements 36 immediately adjacent to the collars 41 and 42 to curve conically toward and remain crossed and unable to come into close apposition and thereby provide openings or interstices 37 therebetween, which remain relatively constant in shape and size so that blood can flow from the first and second ends 32 and 33 through the central or inner flow passage 34 as hereinafter described.

The essentially cylindrical shape of the expansion member when expanded in a radial direction provides an enlarged surface of contact between the expansion member and the vessel wall or obstruction. This enlarged surface of contact enables the cylindrical expansion member to deliver an increased amount of medicament or therapeutic agent which is incorporated within the hydrogel coated on the surface of the flexible elongate elements that comprise the expansion member. This delivery of medicament or therapeutic agent may be by the various well known means previously described electrically active diffusion, pressure, iontophoresis, electroporesis or electro-osmosis.

One example of the means provided in the mechanical dilatation and medicament delivery device 11 for causing relative movement between the first or outer flexible elongate tubular member 12 and the second or inner flexible elongate tubular member 21 and consists of a linear movement mechanism 46. The linear movement mechanism 46 includes a Y-adapter 49 that is provided with a central arm 51 having a lumen 52 through which the second or inner flexible elongate tubular member 21 extends.

It should be appreciated that even though one particular linear movement mechanism 46 has been provided for advancing and retracting the flexible elongate members 12 and 21 with respect to each other, other mechanisms also can be utilized if desired to provide such relative movement. Other possible designs that could be employed are scissors-jack, rachet-type or straight slide mechanisms.

The distal expansion member of the catheter is coated with one or more layers of a hydrogel copolymer material or similar substrate, into which are encapsulated one or more medicaments or therapeutic agents and zero or more electrophoretic carriers. These charged electrophoretic carriers may include by example, sodium lauryl sulfate, phophatidyl choline of various hydrocarbon chain lenghts, bile salts, phospholipids or any of the other charged molecules which would augment the electrophoretic and electro-osmotic processes previously described.

Once the site of obstruction or treatment is reached and the distal cylindrical expansion member is expanded and in contact with the surrounding tissue or vessel wall an electrical charge is applied to the mesh thus driving the therapeutic agent or medicament out of the hydrogel coating and into the target tissue. In this case, the second electrode is placed on the skin of the patient which would act to complete the electrical circuit. The electrical charge applied to the distal mesh and hydrogel coating with encapsulated medicament may be used to cause electrophoretic or electro-osmotic migration of the therapeutic agent or medicament into the target tissues.

As shown in FIGS. 8a-8f, the present invention can employ flow of electrical current in the form of various waveforms to perform the electrophoretic and electro-osmotic procedures. Possible waveforms contemplated for the present invention include square waves, rectangular waves, saw-toothed waves, sinusoidal waves that do not reverse polarity, rectified sinusoidal waves, and other waveform shapes which may reverse polarity but provide a net flow of current in the desired direction.

Electrical current could also be coordinated with the patient's elctrocardiogram such that electrical current is provided only during certain phases of cardiac depolarization. This "gating" of the electrical current would avoid the potential danger of discharging electrical current to the heart during vulnerable phases of depolarization which may lead to cardiac arrhythmias.

Figure 10:
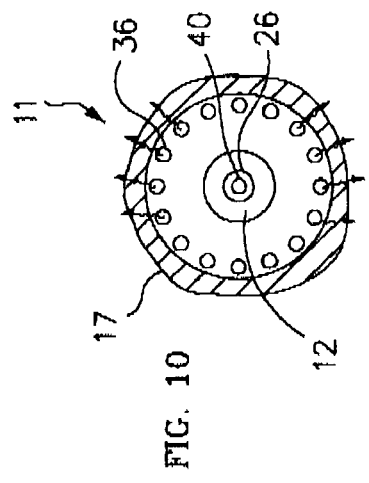
FIG. 10 is a cross sectional view of the flexible elongated elements demonstrating the active electrically mediated dispensing of the hydrogel encapsulated therapeutic agent or medicament into the vessel wall.

As seen in FIG. 10 the flexible elongated elements 36 are designed to be electrically conductive and cause the therapeutic agent or medicament 40 to dispense or migrate into the vessel wall 17.

Figure 11:
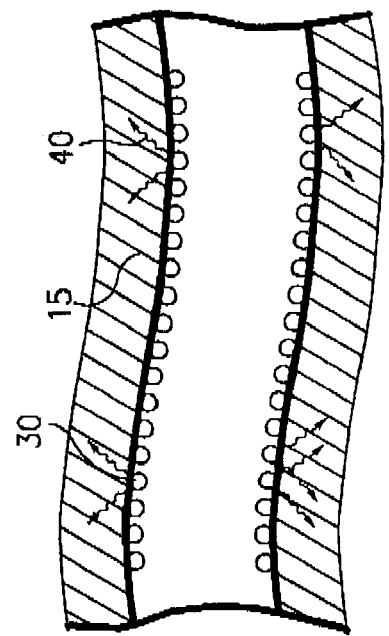
FIG. 11 is another cross sectional side view of the flexible elongated elements and a vessel demonstrating the electrically mediated dispensing of the liposome or micelle-encapsulated therapeutic agent or medicament into the vessel wall.

FIG. 11 is a cross sectional side view of the flexible elongated elements 36 demonstrating the passive or electrically active dispensing of the therapeutic agent or medicament 40 into the vessel wall 17.

Figure 12:
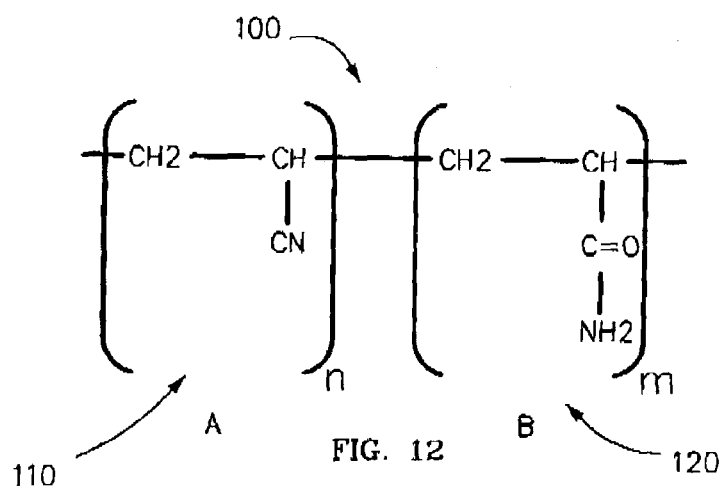
FIG. 12 is a representation of the chemical structure of the multi-block copolymer with two functional groups used to fabricate the hydrogel.

Referring to FIG. 12, the hydrogel copolymer 100 used in this invention is a multi-block copolymer having two functional groups. The first functional group is a hydrophobic nitrile groups 110 and the second function group a hydrophilic amide groups 120. The polyacrylonitrile-polyacrylamide copolymer is converted from the linear polyacrylonitrile. Upon conversion, the linear homopolymer becomes an alternating copolymer. After conversion and in the presence of water, the nitrile groups collapse and the amide groups hydrate and the polymer forms a hydrogel network structure 130, with pores 132 (amide groups) and crosslinks 134 (chain entanglement and nitrile groups).

The conversion process allows the precise control of the degree of conversion and the size of each block. The degree of conversion and the size of each block, among other factors, influence the chemical and physical properties of the resulting hydrogel. The hydrogel for delivery of medicaments in this applications may have a degree of conversion from approximately 55% to 85% which corresponds to approximately 60% to 95% of water content.

The converted block copolymer is dissolved in a suitable solvent at a certain concentration (polymer precursor solution) to generate the desirable viscosity for coating. At this time, the polymer solution is coated onto the catheter. Alternatively, the medicaments or therapeutic agents along with zero or more electrophoretic carriers are mixed with polymer precursor solution before coating. The medicaments or the electrophoretic carriers can be either in the solid form, liquid form or solution form in a suitable solvent. The methodology for thoroughly blending and mixing the medicaments or therapeutic agents or electrophoretic carriers is well known to those skilled art or can be determined by reference to standard references.

Therapeutic agents 40 that can be employed may be anticoagulants, such as D-Phe-Pro-Arg chloromethyl ketone, an RGD peptide-containing compound, heparin, an antithrombin compound, a platelet receptor antagonist, an anti-thrombin antibody, an anti-platelet receptor antibody, aspirin, a prostaglandin inhibitor, a platelet inhibitor, a tissue factor inhibitor, or a tick anti-platelet peptide.

The therapeutic agents 40 can also be a promoter of vascular cell growth, such as a growth factor stimulator, a growth factor receptor agonist, a transcriptional activator, and a translational promoter. Alternatively, the therapeutic agent 40 can be an inhibitor of vascular cell growth, such as a growth factor inhibitor, a growth factor receptor antagonist, a transcriptional repressor, a translational repressor, an antisense DNA, an antisense RNA, a single-stranded DNA molecule, a double-stranded DNA molecule, a single-stranded RNA molecule, a double-stranded RNA molecule, a replication inhibitor, an inhibitory antibody, an antibody directed against growth factors, a bifunctional molecule consisting of a growth factor and a cytotoxin, or a bifunctional molecule consisting of an antibody and a cytotoxin.

The therapeutic agent 40 can be a cholesterol-lowering agent such as atorvastatin, simvistatin, pravastatin and lovastatin, a vasodilating agent, or other agents that interfere with endogenous vasoactive mechanisms. Additionally, the therapeutic agent 40 can be a smooth muscle inhibitor, such as: an agent that modulates intracellular calcium binding proteins; a receptor blocker for contractile agonists; an inhibitor of the sodium/hydrogen antiporter; a protease inhibitor; a vasodilator; a phosphodiesterase inhibitor; a phenothiazine; a compound that increases or mimics endogenous nitrous oxide; a growth factor receptor agonist; an anti-mitotic agent; an immunosuppressive agent; or a protein kinase inhibitor.

In addition, the therapeutic agent 40 can be a smooth muscle inhibitor selected from the group consisting of an agent that modulates intracellular calcium binding proteins, a receptor blocker for contractile agonists, an inhibitor of the sodium/hydrogen antiporter, a protease inhibitor, a nitrovasodilator, a phosphodiesterase inhibitor, a phenothiazine, a growth factor receptor agonist, a growth factor receptor antagonist, an anti-mitotic agent, an immunosuppressive agent, a steroid such as estrogen, hydrocortisone or dexamethasone, and a protein kinase inhibitor, and combinations thereof.

Furthermore, the therapeutic agents 40 employed can be compounds that inhibit cellular proliferation such as Paclitaxel, Rapamycin, Actinomycin D, Methotrexate, Doxorubicin, cyclophosphamide, and 5-fluorouracil, 6-mercapatopurine, 6-thioguanine, cytoxan, cytarabinoside, cis-platin, alcohol, arsenic trioxide, bleomycin, captothecin, capecitabine, carmustine, celecoxib, daunorubicin, docetaxel, etoposide, exemestane, fludarabine, gemcitabine, hydroxyurea, idarubicin, irinotecan, ifosfamide, letrozole, leucovorin, mitoxantrone, pamidronate, pentostatin, porfirmer sodium, streptozotocin, tamoxifen, temozolamide, tenopside, topotecantoremifene, tretinoin, valrubicin, vinorelbine, zoledronate, altretamine, anastrozole, bexarotene, carboplatin, everolimus, chlorambucil, busulfan, and any other drug that can inhibit cell proliferation, and combinations thereof.

To perform as a hydrogel coated device for electrical mediated drug delivery, the distal expansion member will be coated as described in more detail below.

The viscous polymer precursor solution, either by itself or mixed with medicaments with or without charged electrophoretic carriers, is spread onto a clean plastic plate. The mixture is gently mixed using a metal spatula or a glass rod. Upon mixing, the viscous solution is drawn down to a predetermined thickness within a certain surface area. The thickness is related to the desired final coating thickness on the catheter the desired length of coating on the catheter. The distal cylindrical dilating mesh is then rolled over the polymer precursor. A single layer or multiple layers of viscous polymer precursor containing medicaments and electrophoretic carriers are then deposited onto the catheter mesh surface.

Other coating methods may also be employed to deposit a uniform and defined layer of polymer solution onto the surface of the catheter mesh. The conventional coating technology is well known to those skilled in the art or can be determined by reference to standard references.

The coated catheter is then dipped into an appropriate solution to coagulate the polymer to form hydrogel. The solution can be aqueous solution containing electrolytes or other coagulants such as ethanol and water mixtures. The coagulation step converts a viscous polymer precursor solution into a water-swellable hydrogel. Sometimes, a secondary solution is used to remove remaining polar solvent or other non-water coagulants such as ethanol.

The resulting hydrogel polymer structure is a network 130 consisting of pores 132 and crosslinks 134 with the medicaments and zero or more electrophoretic carriers residing in this structure. The pores 132 are connected together through the polymer chain entanglement 134 and through the collapsed hydrophobic nitrile groups 110 which have strong association through their dipolar interactions.

Figure 13:
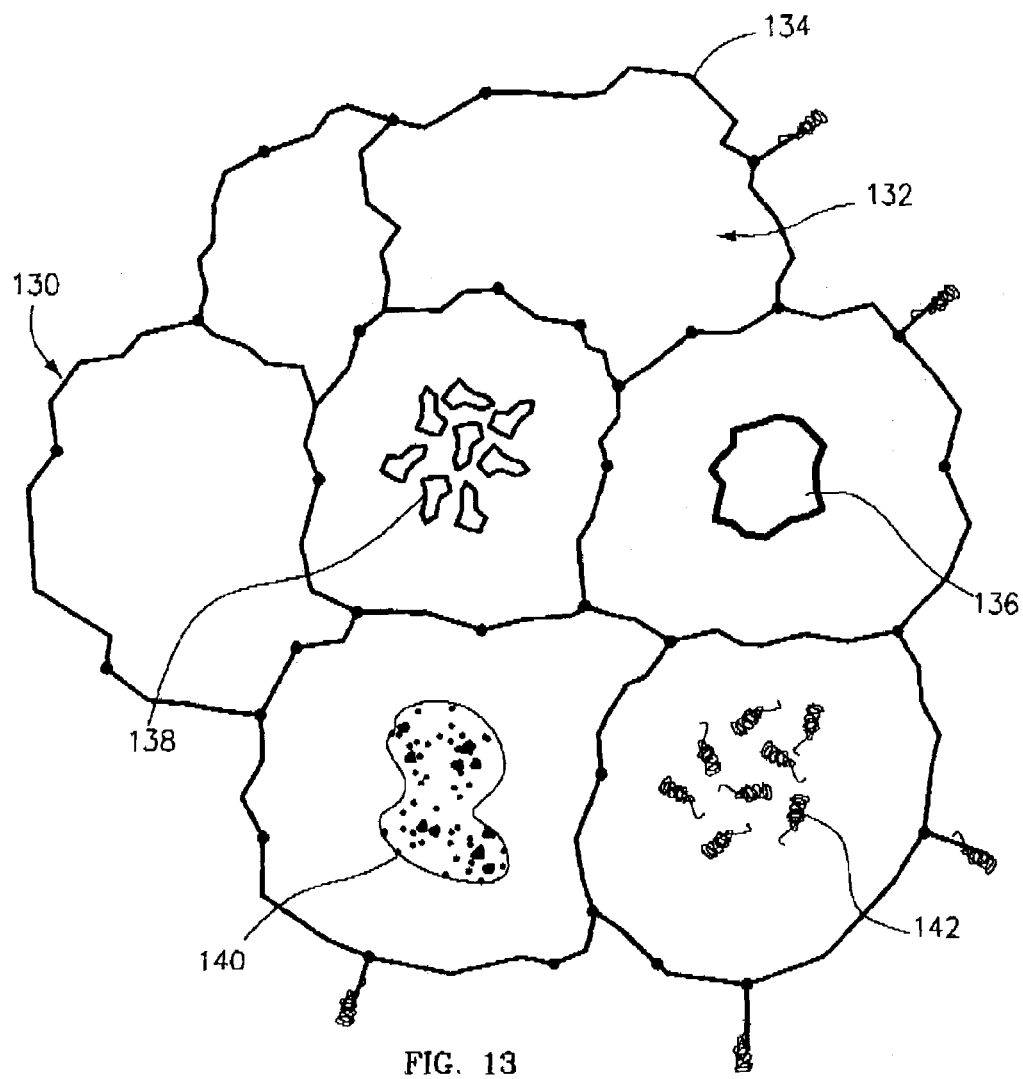
FIG. 13 is a representation of the hydrogel formed network that encapsulates therapeutic agents or medicaments.

The dipolar interactions of the nitrile groups 110 provide the structural integrity of the gel network and the mechanical strength of the hydrogel. The pores 132 (the hydrated amide groups) serve as water channels to transport medicaments and electrophoretic carriers upon the application of electrical energy. FIG. 13 shows the encapsulated medicaments or therapeutic agent as single structure 136, multiple structure 138, precipitates in a solution 140, or as piece of DNA or RNA 142.

The coating can be a one-step operation to coat one layer of hydrogel. However, additional layers serving different purposes may also be added. The additional layers of hydrogel may be of the same kind, or of a different kind, of polymers depending on the desired application For example, a very thin layer of hydrogel may be applied to the catheter mesh surface to promote adhesion. Alternatively, a secondary layer formed of the same or a different hydrogel may be applied to cover the primary coating containing the drugs or medicaments in a manner similar to that described above. This coating may contain zero or more additional drugs or medicaments and zero or more electrophoretic carriers. Depending on application requirements, multiple layers of polymer coating may be used.

One of the purposes of the secondary coating is to retard the passive diffusion of the previously encapsulated drugs or medicaments and electrophoretic carriers into the bloodstream or tissues which may occur prior to the active delivery of the drug or medicaments using electricity.

Operation and use of the polymer coated device for electrically mediated drug delivery 11 may now be briefly described as follows. Let it be assumed that the patient in whom the medical procedure is to be performed utilizing the medicament delivery device 11 has one or more stenoses which at least partially occlude one or more arterial vessels supplying blood to the heart and that it is desired to enlarge the flow passages through these stenoses. Typically the polymer coated device for electrically mediated drug delivery 11 would be supplied by the manufacturer with the cylindrical expansion member 31 in its most contracted position to provide the lowest possible configuration in terms of diameter and so that the diameter approximates the diameter of the outer flexible elongate tubular member 12 and previously coated with a therapeutic agent or medicament 40 and zero or more electrophoretic charged carriers. A means for maintaining the coated expansion member exposed to water will be employed.

Preferably, the coated expansion member 35 should have a diameter that is only slightly greater than the tubular member 12, as for example by 1.0-2.3 millimeters. The first and second collars 41 and 42 also have been sized so they only have a diameter that is slightly greater than the outer diameter of the outer flexible elongate tubular member 12. To bring the cylindrical expansion member 31 to its lowest configuration, the linear movement mechanism 46 has been adjusted so that there is a maximum spacing between the distal extremity 23 of the inner flexible elongate tubular member 21 and the distal extremity 14 of the outer flexible elongate tubular member 12. In this position of the expansion member 31, the flexible elongate elements 36 cross each other at nearly right angles so that the interstices or openings 37 therebetween are elongated with respect to the longitudinal axis.

The polymer coated device for electrical mediated drug delivery 11 is then inserted into a guiding catheter (not shown) typically used in such a procedure and introduced into the femoral artery and having its distal extremity in engagement with the ostium of the selected coronary artery.

The guide wire 26 is then advanced in a conventional manner by the physician undertaking the procedure and is advanced into the vessel containing a stenosis. The progress of the distal extremity of the guide wire 26 is observed fluoroscopically and is advanced until its distal extremity extends distally of the stenosis. With the expansion member 31 in its diametrically contracted position and the hydrogel encapsulated medicament or therpeutic agent coated thereon, the polymer coated device for electrical mediated drug delivery 11 is advanced over the guide wire 26 until the distal end is centered within the region of interest.

After the hydrogel-coated cylindrical expansion member 31 is in a desired position in the stenosis, the cylindrical expansion member 31 is expanded from its diametrically contracted position to an expanded position by moving the distal extremities 14 and 23 closer to each other by operation of the screw mechanism 46. This can be accomplished by holding one distal extremity stationary and moving the other distal extremity towards it or by moving both distal extremities closer to each other simultaneously.

When the hydrogel coated distal cylindrical expansion member 31 is fully expanded it is almost a solid tubular mass which has significant radial strength to fully expand a stenosis or alternatively a stent or prosthesis. Since the expansion member is coated with a hydrogel encapsulating a therapeutic agent or medicament this drug or medicament can be delivered to the vessel during the time of device expansion while blood is permitted to flow unobstructed to the distal vessel.

Now, an electrical charge can be provided to the cylindrical expansion member. This charge will then tend to drive the encapsulated medicaments or therapeutic agents and the zero or more electrophoretic carriers into the tissue through electrophoretic, iontophoretic or electro-osmotic means. The process is known to facilitate or assist the transport of the encapsulated medicament or therapeutic agents and the electrophoretic carriers across the selectively permeable membranes and enhance tissue penetration. Since the present invention involves the use of electrical energy, there are many possible waveforms contemplated for use. As depicted in FIGS. 8a-8f, square waves 61, rectangular waves 63, saw toothed waves 64, sinusoidal waves that do not reverse polarity 65, rectified sinusoidal waves, 72 and modified rectangular or other waves 73. The primary characteristic of the preferred waveforms is that they all provide a net flow of current to the coated expansion member 35. It must be appreciated by those skilled in the art, that the waveforms with frequencies and duty cycles must be capable of delivering the desired current under varying impedances encountered by the expansion member 35 and the surrounding vessel wall 17 and fluids.

After a predetermined time, the electrical current can be altered to achieve another purpose or terminate.

After delivery of the medicaments or therapeutic agent to the lesion has been carried out for an appropriate length of time, the expansion member 31 can be moved from its expanded position to a contracted position.

After the expansion member 31 has been reduced to its contracted or minimum diameter, the polymer coated device for electrically mediated drug delivery 11 can be removed along with the guide wire 26 after which the guiding catheter (not shown) can be removed and the puncture site leading to the femoral artery closed in a conventional manner.

Although, the procedure hereinbefore described was for treatment of a single stenosis or region of interest, it should be appreciated that if desired during the same time another stenosis or region of interest need be treated, the catheter may be advanced to this second area of interest and the procedure repeated. Alternatively, another polymer coated device for electrical mediated drug delivery 11 may be re-inserted in the same or other vessels or regions of interest of the patient and can be treated in a similar manner.

Described below are some examples of experiments conducted using the present invention.

EXAMPLE 1

Local Delivery of Paclitaxel

Preparation of compounded paclitaxol, sodium dodecyl sulfate (SDS) and hydrogel polymer solution precursor for coating.

Prepare stock solutions of paclitaxol and SDS in the solvent of dimethyl sulfoxide (DMSO) at the concentration of 0.5 mg/ul for paclitael in DMSO and 0.6 mg/ul for SDS in DMSO. Weigh 433 mg of hydrogel solution onto a clean plastic plate having two elevated spacers at 0.5 mm height and separated by 2 cm. Add 81.3 ul of SDS stock solution, or 48.8 mg of SDS, and 97.5 ul of Paclitaxel stock solution, or 48.8 mg of Paclitaxel onto the hydrogel polymer solution. Mix well with a spatula. Upon mixing, spread the viscous mix evenly with the spatula or a glass rod within the confines of the two spacers. Use both gloved hands to hold both ends of the catheter mesh portion and roll the mesh gently over the viscous polymer mix once, or twice if necessary. This coating is designated to contain 5% paclitaxel and 5% SDS using the initial weight of polymer mix as a reference.

When the coating is completed, the mesh portion of the catheter is dipped into 3 ml of trisborate buffer for 3 minutes to coagulate the polymer solution into gel. After 3 minutes, the mesh portion of the catheter is removed from the coagulation solution and ready for use.

EXAMPLE 2

Local Delivery of E2F Decoy

Preparation of compounded E2F Decoy, sodium dodecyl sulfate (SDS) and hydrogel polymer solution precursor for coating.

Prepare SDS stock solution in the solvent of dimethyl sulfoxide (DMSO) at the concentration of 0.6 mg/ul. Weigh 747 mg of hydrogel solution onto a clean plastic plate having two elevated spacers at 0.5 mm height and separated by 5 cm. Add 69.8 mg of E2F Decoy and 70 ul of DMSO. Mix well. Add 35 ul of SDS stock solution (or 21 mg of SDS). Mix well with the spatula. Upon mixing, spread the viscous mix evenly with the spatula or a glass rod within the confines of the two spacers. Use both gloved hands to hold both ends of the catheter mesh portion and roll the mesh gently over the viscous polymer mix once, or twice if necessary. This coating is designated to contain 7.5% paclitaxel and 2.25% SDS using the initial weight of polymer mix as a reference.

When the coating is completed, the mesh portion of the catheter is dipped into 13 ml of ethanol/water solution containing 75% ethanol and 25% water for 1 minutes. Following the coagulation, the mesh is dipped into a second solution for 2 minutes. The second solution is 13 ml of saline containing 20% glycerol. After completing the immersion for 2 minutes in the second solution, the mesh portion of the catheter is removed from the coagulation solution and ready for use.

In an experiment to measure the amount of taxol released, the catheter was placed in an electrolytic cell and discharged at a current of 10 milliamps and a voltage of 10 volts. The solution was analyzed for paclitaxel concentration. There was minimal paclitaxel release without power, but a significant increase of the release of paclitaxel with power. In another experiment, catheters loaded with a fluorescent paclitaxel compound (Oregon Green paclitaxel) were placed into isolated coronary arteries. The catheter was expanded and current (10 millamps, 10 volts) for 10 minutes. The arterial segment with no power had the fluorescent compound limited to the luminal surface that was in contact with the catheter, consistent with little or no movement of the paclitaxel. In the arterial segment treated with power, the fluorescent compound was seen throughout the artery, consistent with movement of the fluorescent compound through the arterial wall.

In an experiment to measure the amount of taxol released, the catheter was placed in an electrolytic cell and discharged at a current of 10 milliamps and a voltage of 10 volts. The solution was analyzed for paclitaxel concentration. There was minimal paclitaxel release without power, but a significant increase of the release of paclitaxel with power. In another experiment, catheters loaded with a fluorescent paclitaxel compound (Oregon Green paclitaxel) were placed into isolated coronary arteries. The catheter was expanded and current (10 millamps, 10 volts) for 10 minutes. The arterial segment with no power had the fluorescent compound limited to the luminal surface that was in contact with the catheter, consistent with little or no movement of the paclitaxel. In the arterial segment treated with power, the fluorescent compound was seen throughout the artery, consistent with movement of the fluorescent compound through the arterial wall. consistent with movement of the fluorescent compound through the arterial wall.

EXAMPLE 3

Iontophoretic Release of Paclitaxel

In an experiment to measure the amount of taxol released, a mesh segment that was coated with a hydrogel that was loaded with paclitaxel according to the procedure described in Example 1 was placed in an electrolytic cell and discharged at a current of 10 milliamps and a voltage of 10 volts for 10 minutes. The solution was then analyzed for paclitaxel concentration by high performance liquid chromatography. As shown in FIG. 1, there was minimal paclitaxel release without power, but a significant increase of the release of paclitaxel with power.

EXAMPLE 4

Iontophoretic Delivery of Pacltaxel into Isolated Coronary Arteries

Catheters with mesh segments that were coated with a hydrogel that was loaded with a fluorescent paclitaxel compound (Oregon Green paclitaxel) were placed into isolated coronary arteries. The catheter was expanded and current (10 millamps, 10 volts) for 10 minutes. As seen in FIG. 2, the arterial segment with no power had the fluorescent compound limited to the luminal surface that was in contact with the catheter, consistent with little or no movement of the paclitaxel. In the arterial segment treated with power, the fluorescent compound was seen throughout the artery, consistent with movement of the fluorescent compound throughout the arterial wall.

EXAMPLE 5

Iontophoretic Release of E2F Decoy

In an experiment to measure the amount of E2F decoy released, a mesh segment that was coated with a hydrogel that was loaded with E2F decoy according to the procedure described in Example 4 was placed in an electrolytic cell and discharged at a current of 10 milliamps and a voltage of 10 volts for 10 minutes. The solution was then analyzed for E2F decoy concentration by ultravioilet spectrophotometry. As shown in FIG. 3, there was minimal E2F decoy release without power, but a significant increase of the release of E2F decoy with power.

EXAMPLE 6

Iontophoretic Delivery of E2F Decoy into Isolated Coronary Arteries

Catheters with mesh segments that were coated with a hydrogel that was loaded with a fluorescent E2F Decoy compound (Bodipy-labeled E2F Decoy) were placed into isolated coronary arteries. The catheter was expanded and current (10 millamps, 10 volts) for 10 minutes. As seen in FIG. 4, the arterial segment with no power had the fluorescent compound limited to the luminal surface that was in contact with the catheter, consistent with little or no movement of the E2F Decoy. In the arterial segment treated with power, the fluorescent compound was seen throughout the artery, consistent with movement of the fluorescent compound throughout the arterial wall.

We claim:

1. An apparatus for delivering a therapeutic agent or medicament to an obstruction within a vascular segment or a body passageway which comprises:
   a catheter having a proximal and a expandable distal end, said expandable distal end comprising a cylindrically shaped expansion member located on the distal end of the catheter, the expansion member including first and second ends and having a plurality of flexible elongated elements, the plurality of flexible elongate elements comprising a first set of elements having a first common direction of rotation crossing a second set of elements having a second common direction of rotation opposite to that of the first direction of rotation to form a double helix mesh,
   said catheter further comprising:
      a means for conducting electrical energy from a proximal end to said expandable distal end;
      a first elongate member defining a first lumen; and
      a second elongate member defining a second lumen, which is located within the first lumen, to receive a guide wire,
      wherein the second elongate member is centrally disposed within a space formed by the expansion member,
      wherein the means for conducting electrical energy from the proximal end to the expandable distal end comprises at least one electrical lead located within the first lumen, said at least one electrical lead is positioned within the second elongate member located within the first lumen,
   said distal end incorporating a hydrogel polymer encapsulated with a therapeutic agent or medicament and electrophoretic or electro-osmotic carriers.

2. An apparatus as recited in claim 1, wherein said catheter with hydrogel encapsulated with a therapeutic agent or medicament will function to release the therapeutic agent or medicament-from the hydrogel by electrophoretic, iontophoretic or electro-osmotic means.

3. An apparatus as recited in claim 1, wherein said catheter with hydrogel encapsulated with a therapeutic agent or medicament will function to deliver the therapeutic agent or medicament-into target tissues of said vascular segment or body passageway by electrophoretic, iontophoretic or electro-osmotic means.

4. An apparatus as recited in claim 1, wherein said hydrogel encapsulated with a therapeutic agent or medicament is an anticoagulant selected from the group consisting of D-Phe-Pro-Arg chloromethyl ketone, an RGD peptide-containing compound, heparin, an antithrombin compound, a platelet receptor antagonist, an anti-thrombin antibody, an anti-platelet receptor antibody, hirudin, hirulog, phe-pro-arg-chloromethyketone (Ppack), Factor VIIa, Factor Xa, aspirin, clopridogrel, ticlopidine, a prostaglandin inhibitor, a platelet inhibitor, a tissue factor inhibitor, and a tick anti-platelet peptide, and combinations thereof 5. An apparatus as recited in claim 1, wherein said hydrogel encapsulated with a therapeutic agent or medicament is a promoter of vascular cell growth selected from the group consisting of a growth factor stimulator, a growth factor receptor.

6. An apparatus as recited in claim 1, wherein said hydrogel encapsulated with a therapeutic agent or medicament is an inhibitor of vascular cell growth selected from the group consisting of a growth factor inhibitor, a growth factor receptor antagonist, a transcriptional repressor, a translational repressor, an antisense DNA, an antisense RNA, synthetic DNA compounds, especially those with backbones that have been modified to inhibit enzymatic degradation (e.g. phosphorothioate compounds and morpholino diamidate compounds), a replication inhibitor, an inhibitory antibody, an antibody directed against growth factors, a bifunctional molecule consisting of a growth factor and a cytotoxin, and a bifunctional molecule consisting of an antibody and a cytotoxin, double stranded DNA, single stranded DNA, single stranded RNA and a double stranded RNA, a single-stranded DNA molecule, a double-stranded DNA molecule, a single-stranded RNA molecule, a double-stranded RNA molecule, and combinations thereof.

7. An apparatus as recited in claim 1, wherein said hydrogel encapsulated with a therapeutic agent or medicament is selected from the group consisting of a cholesterol-lowering agent, a vasodilating agent, and agents which interfere with endogenous vasoactive mechanisms, estrogen, testosterone, steroid hormones, cortisol, dexamethasone, corticosteroids, thyroid hormones, thyroid hormones analogs, throid hormones antagonist, adrenocorticotrophic hormone, thyroid stimulating hormone, thyroid releasing factor, thyroid releasing factor analogs, thyroid releasing factor antagonists and combinations thereof.

8. An apparatus as recited in claim 1, wherein said hydrogel encapsulated with a therapeutic agent or medicament is a smooth muscle inhibitor selected from the group consisting of an agent that modulates intracellular calcium binding proteins, a receptor blocker for contractile agonists, an inhibitor of the sodium/hydrogen antiporter, a protease inhibitor, a nitrovasodilator, a phosphodiesterase inhibitor, a phenothiazine, a growth factor receptor agonist, an anti-mitotic agent, a growth factor receptor antagonist, an immunosuppressive agent, a steroid such as estrogen, hydrocortisone or dexamethasone, and a protein kinase inhibitor, and combinations thereof.

9. An apparatus as recited in claim 1, wherein said hydrogel encapsulated with a therapeutic agent or medicament is a compound that inhibits cellular proliferation, Paclitaxel, Rapamycin, Actinomycin D, Methotrexate, Doxorubicin, cyclophosphamide, and 5-fluorouracil, 6-mercapatopurine, 6-thioguanine, cytoxan, cytarabinoside, cis-platin, alcohol, arsenic trioxide, bleomycin, captothecin, capecitabine, carmustine, celecoxib, daunorubicin, docetaxel, etoposide, exemestane, fludarabine, gemcitabine, hydroxyurea, idarubicin, irinotecan, ifosfamide, letrozole, leucovorin, mitoxantrone, pamidronate, pentostatin, porfirmer sodium, streptozotocin, tamoxifen, temozolamide, tenopside, topotecantoremifene, tretinoin, valrubicin, vinorelbine, zoledronate, altretamine, anastrozole, bexarotene, carboplatin, everolimus, chlorambucil, busulfan, and any other drug that can inhibit cell proliferation, and combinations thereof.

10. An apparatus as recited in claim 1, wherein said hydrogel encapsulated with a therapeutic agent or medicament will migrate into target tissues when exposed to an electrical energy applied by an electrical delivery device.

11. An apparatus as recited in claim 1, wherein said hydrogel encapsulated with a therapeutic agent or medicament is a combination of one or more medicaments.

12. An apparatus as recited in claim 1, wherein said catheter with hydrogel encapsulated with a therapeutic agent or medicament is an over-the wire design.

13. An apparatus as recited in claim 1, wherein said catheter with hydrogel encapsulated with a therapeutic agent or medicament employs a rapid exchange design.

14. An apparatus as recited in claim 1 further comprising by a first contracted configuration and a second expanded configuration wherein an inner flow passage positioned between the catheter and cylindrically shaped expansion member is adapted to allow blood perfusion while said expansion member is in either in said first contracted configuration or in said second expanded configuration.

15. A method for delivering a therapeutic agent or medicament to an obstruction in a body passageway which comprises the steps of:

advancing a catheter for electrically mediated drug delivery to a predetermined site with a body passageway, said catheter having an substantially cylindrical expansion member coated with a hydrogel encapsulated with therapeutic agent or medicament, said expansion member including first and second ends and having a plurality of flexible elongated elements, the plurality of flexible elongate elements comprising a first set of elements having a first common direction of rotation crossing a second set of elements having a second common direction of rotation opposite to that of the first direction of rotation to form a double helix mesh, the catheter including a first elongate member defining a first lumen and a second elongate member defining a second lumen, wherein the second elongate member is located within the first lumen, wherein the second lumen is adapted to receive a guide wire, wherein the second elongate member is centrally disposed within a space formed by the expansion member, and wherein at least one electrical lead is positioned within the second elongate member located within the first lumen; and applying a force on said expansion member to axially displace the first and second sets of elements relative to one another so that the expansion member moves between a first contracted configuration and a second expanded configuration wherein said obstruction dilates said obstruction in a body passageway and delivers the encapsulated with therapeutic agent or medicament substantially along the entire length of said expansion member to an said obstruction in the body passageway.

16. A method as recited in claim 15 which further comprises the step of positioning a guidewire in the body passageway, and wherein said advancing step is accomplished by threading said expansion member over said guidewire.

17. A method as recited in claim 15 which further comprises the step of allowing said expansion member to be in said second expanded configuration for a predetermined period of time after the dilatation step to further expose said obstruction to the therapeutic agent or medicament.

* * * * *

UNITED STATES PATENT AND TRADEMARK OFFICE
CERTIFICATE OF CORRECTION

| | | |
|---|---|---|
| PATENT NO. | : 7,517,342 B2 | Page 1 of 2 |
| APPLICATION NO. | : 10/425170 | |
| DATED | : April 14, 2009 | |
| INVENTOR(S) | : Scott et al. | |

It is certified that error appears in the above-identified patent and that said Letters Patent is hereby corrected as shown below:

Column 1, line 44, "in U.S. Pat." should be changed to --U.S. Pat.--;
Column 1, line 63, "means passive" should be changed to --means, passive--;
Column 2, line 46, "suspensions which" should be changed to --suspensions (which--;
Column 2, lines 64-65, "compounds may oftern" should be changed to --compounds and may often--;
Column 3, line 21, "medicaments is can be" should be changed to --medicaments can be--;
Column 3, line 24, "but no exclusively" should be changed to --but not exclusively--;
Column 3, line 34, "structures These" should be changed to --structures. These--;
Column 3, line 35, "agents" should be changed to --agents.--;
Column 3, line 46, "a apparatus" should be changed to --an apparatus--;
Column 3, line 50, "a apparatus" should be changed to --an apparatus--;
Column 4, line 23, "factors Migration" should be changed to --factors. Migration--;
Column 4, line 64, "polyelectrolyts" should be changed to --polyelectrolytes--;
Column 4, lines 64-65, "phospholipids ..." should be changed to --phospholipids--;
Column 5, line 25, "electode" should be changed to --electrode--;
Column 5, line 57, "hydrogl" should be changed to --hydrogel--;
Column 6, line 58, "FIGS. 1-9" should be changed to --FIGS. 1-8--;
Column 8, line 14, "and have generally" should be changed to --and generally--;
Column 8, lines 26-27, "as a over-the-wire" should be changed to --as an over-the-wire--;
Column 9, line 50, "described electrically" should be changed to --described: electrically--;
Column 10, line 6, "phophatidyl" should be changed to --phosphatidyl--;
Column 10, line 7, "lenghts," should be changed to --lengths,--;
Column 10, line 13, "wall an" should be changed to --wall, an--;
Column 10, line 17, "patient which" should be changed to --patient, which--;
Column 10, line 32, "elctrocardiogram" should be changed to --electrocardiogram--;
Column 10, line 49, "function group" should be changed to --functional group--;
Column 10, line 63, "applications" should be changed to --application--;
Column 10, line 64, "85% which" should be changed to --85%, which--;
Column 11, line 10, "skilled art" should be changed to --skilled in the art--;
Column 12, line 53, "application For" should be changed to --application. For--;
Column 13, line 9, "delivery 11" should be changed to --delivery--;
Column 13, line 65, "medicament this" should be changed to --medicament, this--;

Signed and Sealed this

Twentieth Day of July, 2010

David J. Kappos
*Director of the United States Patent and Trademark Office*

CERTIFICATE OF CORRECTION (continued)
U.S. Pat. No. 7,517,342 B2

Column 14, line 50, "paclitaxol should be changed to --paclitaxel--;
Column 14, line 53, "paclitaxol" should be changed to --paclitaxel--;
Column 14, line 55, "0.5 mg/ul" should be changed to --0.5 mg/µl--;
Column 14, line 55, "paclitael" should be changed to --paclitaxel--;
Column 14, line 55, "0.6 mg/ul" should be changed to --0.6 mg/µl--;
Column 14, line 58, "81.3 ul" should be changed to --81.3 µl--;
Column 14, line 59, "97.5 ul" should be changed to --97.5 µl--;
Column 15, line 16, "0.6 mg/ul" should be changed to --0.6 mg/µl--;
Column 15, line 19, "70 ul" should be changed to --70 µl--;
Column 15, line 20, "35 ul" should be changed to --35 µl--;
Column 15, lines 44-45, "current" should be changed to --current was applied--;
Column 15, line 53, column 16, line 3, the duplicate paragraph should be deleted;
Column 16, line 23, "Pacltaxel" should be changed to --Paclitaxel--;
Column 16, line 28, "current" should be changed to --current was applied--;
Column 16, line 49, "ultravioilet" should be changed to --ultraviolet--;
Column 16, line 62, "current" should be changed to --current was applied--;
Column 17, line 8 (claim 1, line 4), "a expandable" should be changed to --an expandable--;
Column 17, line 56 (claim 4, line 8), "ethyketone" should be changed to --ethylketone--;
Column 19, line 2 (claim 14, line 2), "by a first" should be changed to --a first--; and
Column 20, line 15 (claim 15, line 33), "to an said" should be changed to --to said--.